United States Patent [19]
Milligan et al.

[11] 3,936,357
[45] Feb. 3, 1976

[54] METHOD AND DEVICE FOR DETERMINING THE CONCENTRATION OF A SUBSTANCE IN A FLUID

[75] Inventors: Terry W. Milligan, Belmont; Richard F. Wright, Acton, both of Mass.

[73] Assignee: Polaroid Corporation, Cambridge, Mass.

[22] Filed: Aug. 16, 1974

[21] Appl. No.: 498,059

[52] U.S. Cl. ................... 195/103.5 R; 195/103.5 C
[51] Int. Cl.² .......................................... G01N 31/14
[58] Field of Search... 195/103.5, 103.5 R, 103.5 C; 23/253 TP

[56] References Cited
UNITED STATES PATENTS

| | | | |
|---|---|---|---|
| 3,690,836 | 9/1972 | Buissiere | 195/103.5 |
| 3,723,064 | 3/1973 | Liotta | 23/253 TP |
| 3,783,105 | 1/1974 | Moyer et al. | 23/253 TP |
| 3,785,930 | 1/1974 | Ellis | 195/103.5 |
| 3,791,933 | 2/1974 | Moyer et al. | 23/253 TP |

Primary Examiner—A. Louis Monacell
Assistant Examiner—Esther L. Massung
Attorney, Agent, or Firm—Philip G. Kiely

[57] ABSTRACT

A diagnostic test device comprising an absorbent medium adapted to receive and retain a measured amount of fluid containing the substance to be tested and reagents adapted to contact said fluid to provide a visual determination of the presence and/or concentration of the substance, wherein the absorbent medium comprises a substantially non-swellable material of substantially uniform and constant porosity and thickness.

8 Claims, 3 Drawing Figures

U.S. Patent   February 3, 1976   3,936,357
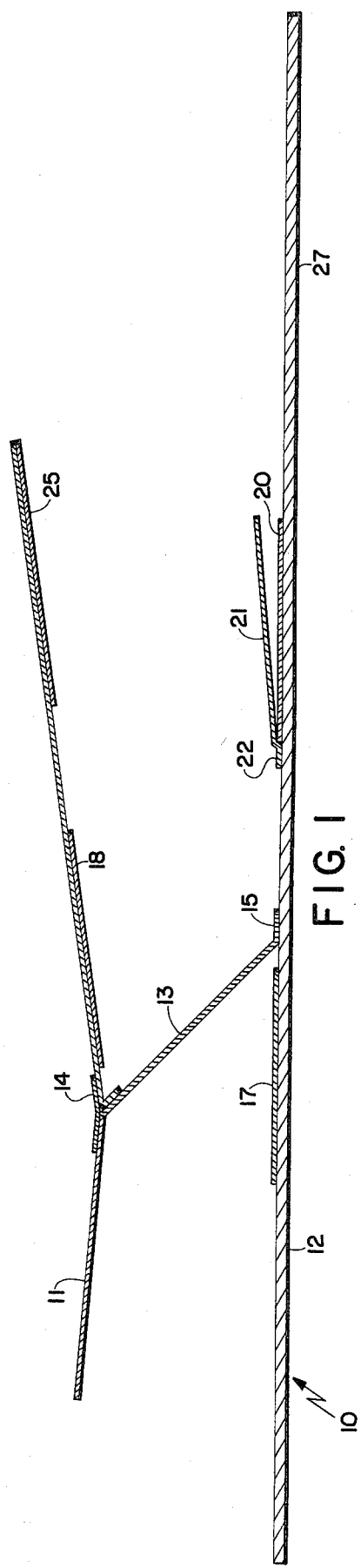
FIG. 1
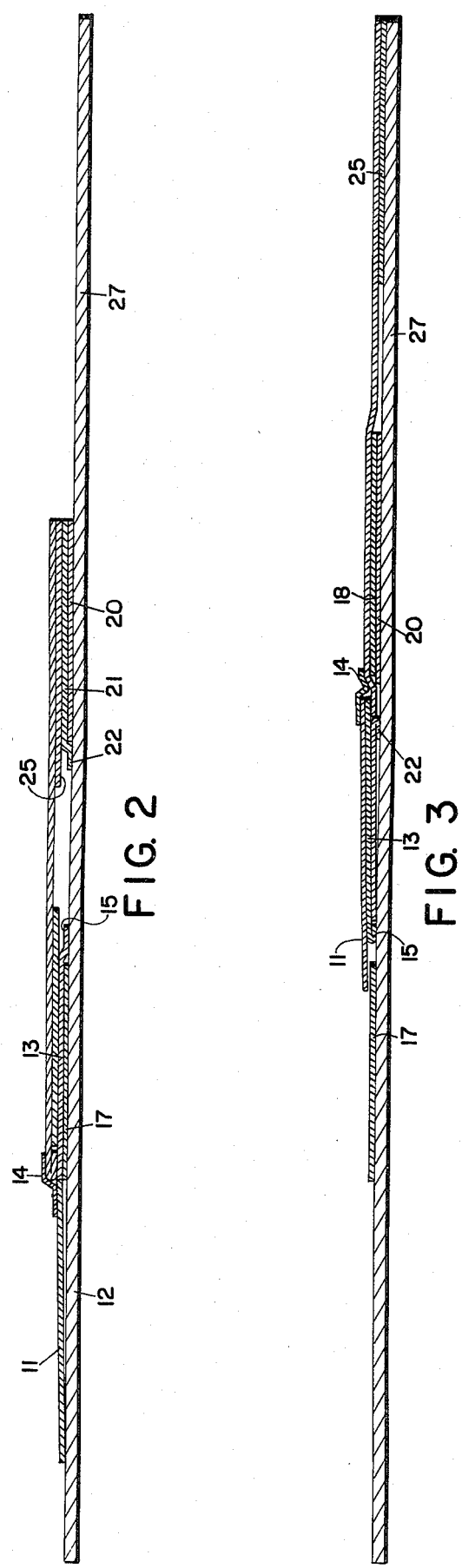
FIG. 2
FIG. 3

METHOD AND DEVICE FOR DETERMINING THE CONCENTRATION OF A SUBSTANCE IN A FLUID

BACKGROUND OF THE INVENTION

A variety of devices are known today for analysis of body fluids such as urine, blood, etc. Such devices generally employ extremely accurate procedures and provide a valuable diagnostic tool. However, most such devices are expensive, require trained personnel and involve time-consuming techniques. Obviously, such devices are unavailable for use by a layman in, for example, daily monitoring of a diabetic condition.

To fill this very important need a number of relatively simple devices and test strips have been developed and marketed. Many of the so-called simple devices developed for use by untrained personnel suffer from a variety of deficiencies. Accuracy, the ability of the operator to discern relatively minor changes and ease of use are some of the problems encountered with such prior art devices.

SUMMARY OF THE INVENTION

The present invention is directed to a relatively simple diagnostic test device wherein a predetermined quantity of fluid containing the substance to be tested is contacted with suitable reagents which will provide a visual, preferably colorimetric determination of the presence and/or concentration of the substance. The predetermined quantity is provided by an absorbent material of uniform and constant porosity and thickness. The present invention is also concerned with preferred devices employing such absorbent materials.

One of the principal problems of such devices involves the accurate metering of the fluid to provide an accurate determination of the substance under test. Pipettes, syringes and the like are expensive, bulky, require some degree of skill and care in use and are frequently fragile.

It is an object of the present invention to provide techniques and devices not susceptible to the deficiencies of the prior art.

BRIEF DESCRIPTION OF THE DRAWINGS

FIG. 1 is an enlarged, cross-sectional view of the testing device of the present invention;

FIG. 2 is an enlarged, cross-sectional view of the testing device of FIG. 1 in the first stage of operation; and FIG. 3 is an enlarged, cross-sectional view of the device of FIG. 1 in the second stage of operation.

DETAILED DESCRIPTION OF THE INVENTION

The present invention is directed to a relatively simple diagnostic test device for use in analyzing a substance contained in a body fluid.

As stated above, one of the principal drawbacks in employing sufficiently reliable diagnostic test devices involves the difficulty in accurately introducing the specific amount of body fluid into contact with the reagents which will provide the quantitative determination.

By means of the present invention, an accurate amount of fluid is made available for analysis by employing an absorbent material of uniform and constant porosity as the receiving medium for the fluid. The aforementioned material will receive and retain a predetermined amount which then can be expelled into a reaction zone by exerting a compressive force thereon, or alternatively, the reactants adapted to provide the visual determination of the substance are introduced into the material with the analytical reaction occurring therein.

Thus, by means of the present invention, analysis of substances in blood, urine, etc., can be carried out quickly and easily without the need of trained personnel to provide an accurate measure of the substance under consideration in a body fluid.

Materials suitable for use in the present invention as an absorbent material are well known to the art.

In a preferred embodiment of the present invention, the above-described absorbent medium is disposed between and attached to first and second sheets in substantially parallel relationship. The absorbent medium is pivotally attached at its leading and trailing edges, respectively, to said first and second sheets. At least one of said first and second sheets contain reagents to provide the determination of the substance under test, said reagents adapted to contact said absorbent medium when the first and second sheets are moved into a superposed first position. The first and second sheets are then movable to a superposed second position where reaction products formed in said first sheet contact indicator means to provide a visual determination of the substance.

Thus, in operation, fluid is applied to the absorbent medium intermediate the first and second sheets. As stated above, the nature of the absorbent medium permits the retention of a predetermined, accurate quantity of fluid. The sheets are then moved into a first superposed position, sandwiching the absorbent medium in contact with said sheets. The fluid in the absorbent means contacts reagents disposed on one or preferably both of said sheets. The reaction products produced by the reagents and the substance in the fluid are formed in the first sheet adjacent the absorbent medium. After sufficient time has elapsed for the reaction, the sheets are moved to a second superposed position by pivoting the sheets around the absorbent medium, contacting the aforementioned reaction products with visual indicator means, where the quantity or presence of the substance can be ascertained by inspection.

In one embodiment, the visual determination is a colorimetric determination and is viewed through a transparent portion of one of the sheets and compared against a standard scale, either attached to the test device or separate therefrom. By matching the color produced in the test device with the scale, an accurate determinatiion is readily available. The test device may then be discarded. Since a measured amount of fluid is contacted with a premeasured amount of reactants, a quantitative determination is achieved.

In an alternative embodiment, the second or indicator position includes a precipitation chromatograph. Thus, the reaction products, when the sheets are moved into the second position, would be eluted by a solvent and diffused into a chromatographic medium which contains a compound which forms an insoluble, colored compound upon contact with the reaction product produced from the substance. Since the colored material is insoluble and thus not diffusible, the only compound moving up the chromatographic medium would be the aforementioned reaction products. As the reaction product is converted to a nonreactable form, the colored wave front on the chromatographic medium is halted and the length of the colored zone measured by an appropriate standard scale to provide a quantitative determination of the substance under test.

To describe the operation of the diagnostic test device in more detail, the operator will expose the absorbent fluid receiving medium, preferably by lifting a portion of one of the sheets, and place the fluid containing the substance to be tested on the absorbent material. It is not necessary to apply a measured amount; it is only necessary that the absorbent medium be saturated. As stated above, the construction of the absorbent medium will provide for the retention of a predetermined quantity of fluid.

The first and second sheets are then moved into superposed relationship to a first position with the absorbent medium in contacting relationship therebetween. Preferably, pressure is applied to the device to expel excess fluid from the absorbent medium and enable the reaction to be carried out in zones of the sheets.

Pressure is preferably applied by moving the device relative to and between a pair of juxtaposed members. These members may comprise a pair of substantially parallel rollers, a roller and a plate or any other apparatus that will, as the device is moved through it, force the fluid from the absorbent medium. Alternatively, rollers may be moved relative to the device.

The test reagents which are adapted to react with the substance being tested for are disposed on the inner surfaces of the first and second sheets in contact with the absorbent medium when the device is in the first position. The substance in the fluid undergoes reactions which provide reaction products capable of being measured by means described above. These reaction products are formed and retained in the first sheet adjacent the absorbent medium in the first position.

The test device is moved to the second position where the reaction products contact the colorimetric determination means, e.g., a colorimetric indicator or precipitation chromatograph. Preferably, the reactants comprise enzymes, coenzymes and a colorimetric indicator.

Turning now to the drawings, a preferred diagnostic test device is shown in each step of the operation.

The diagnostic test device 10 of the present 13 is composed of absorbent medium 18 pivotally attached at the ends to first sheet 11 at point 14 and second sheet 12 at point 15. First sheet 11 carries on an inner surface reagent layer 18 adapted to react with the substance under test, preferably enzymes and coenzymes and also carries, adjacent an end thereof, colorimetric determination means 25 in the embodiment shown a precipitation chromatographic sheet. Second sheet 12 carries on an inner surface reagent layer 17, preferably enzymes adapted to provide the abovedescribed reaction, as well as an eluting solvent layer 20, preferably in a semi-swollen gel. In order to protect the semi-swollen gel a cover sheet 21 is pivotally attached to second sheet 12 at point 22. A transparent portion 27 of second sheet 12 enables the viewing of the colorimetric determination as described below.

In operation, a section of first sheet 11 is pivoted, exposing absorbent medium 13 and the fluid containing the substance to be tested is applied thereto. The diagnostic test device is then moved to a first superposed position as shown in FIG. 2 with layer 18 of sheet 11 and layer 17 of sheet 12 in contact with absorbent means 13. When the reagents of layers 18 and 17 react with the substance in the fluid, the reaction products are formed in layer 18. After permitting the necessary time to elapse for the reactions to occur, the diagnostic test device is moved to a second superposed position whereby layer 18 contacts the eluting solvent in layer 20. The cover sheet 21 is retracted exposing layer 20 prior to moving the device to said second position. The solvent in layer 20 would dissolve the reaction products of layer 18, carrying them down the chromatographic sheet where a colored moiety would be generated providing the numerical determination of the concentration of the substance.

It may be desirable to remove some components of the fluid prior to contacting the fluid with the reactants. Such components may be removed by superposing a filter over the absorbent means to remove the components from the test area. Alternatively, precipitants may be employed in the absorbent medium itself. Protein is one example of a component of the fluid that may be removed prior to the reaction.

The sheets which comprise the walls of the device are preferably transparent and may be composed of any suitable material which will retain the reactants without leakage or without interfering with the reaction.

As stated above, the novel device of the present invention may be employed for a variety of diagnostic tests. For example, hemoglobin in blood may be ascertained by application of a blood sample to the absorbent material and disposing an oxidizing agent and a suitable indicator intermediate the superposed sheets. Suitable indicators are known to the art for such a test.

The novel test device of the present invention is particularly suitable for the enzymatic analysis of glucose in body fluids. The test for glucose is based on the following reaction sequence:

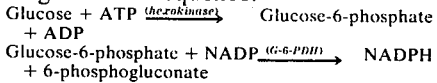

Glucose + ATP → Glucose-6-phosphate + ADP

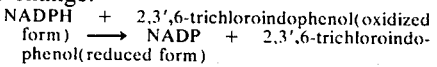

Glucose-6-phosphate + NADP → NADPH + 6-phosphogluconate

The absorption of NADPH at 340 nm is a measure of the glucose content in the sample fluid. Since 340 nm is beyond the visible region of the electromagnetic spectrum, a suitable indicator may be included in the system which will react with NADPH to give a suitable color change.

NADPH + 2,3',6-trichloroindophenol(oxidized form) → NADP + 2,3',6-trichloroindophenol(reduced form)

ATP = Adenosine triphosphate
ADP = Adenosine diphosphate
NADP = Nicotinamide adenine dinucleotide phosphate
NADPH = Nicotinamide adenine dinucleotide phosphate reduced
G-6-PDH = Glucose-6-phosphate dehydrogenase The body fluid containing the glucose would be applied to the absorbent material. The reactants, ADP and NADP would be located intermediate the sheets, preferably coated thereon. Suitable indicators include methylene blue, the sodium salt of 3'-chloroindophenol, the sodium salt of 2,3'-trichloroindophenol and the sodium salt of 2,6-dichloroindophenol and would be located on a sheet adapted to contact the reaction products derived from the fluid, ADP and NADP. In a preferred embodiment, precipitation chromatography was employed using the ferric complex of 4,7-diphenyl-1,10-phenanthroline to form an insoluble colored product upon reacting with NADPH. It may be desirable to apply suitable time delay layers, e.g., polymeric layers of specific solubility or permeability, to one or more of the reactants to ensure the order of reaction. The color generated by the reaction will be compared visually with suitable color reference standards.

In a preferred embodiment, the ATP and NADP and/or enzymes would be applied to layers 17 and 18 and water in a semi-swollen gel would be coated on layer 20. The ATP and NADP and/or enzymes may be disposed in the reaction zone just prior to application of the compressive force. However, in a particularly preferred embodiment, the enzymes are in a stable, immobilized state which, upon contact with the fluid to be tested, is activated. NADH would be generated in layer 18 and then eluted therefrom by the water in layer 20. The concentration of the NADH would be determined by the height of the colored column in the chromatographic sheet.

If the fluid to be analyzed contains a reducing substance (e.g., ascorbic acid in urine), it is preferred to employ a colorimetric indicator system that does not rely on a redox system to avoid any interference in the determination or inaccurate readings. For example, in a glucose determination a suitable indicator system may comprise a ferric salt, such as ferric nitrate coated on silica gel. A ferric-NADH salt is formed which is purple. While the thus-formed colorimetric determination is suitable for the aforementioned glucose determination, if a permanent record of the test is desired then 1,10-phenanthroline or 4,7-diphenyl-1,10-phenanthroline also coated on the silica gel will provide a pink, permanent colorimetric indication.

In still another embodiment, in addition to the above-mentioned time delay layers, the reactants may be disposed in a suitable polymeric material and a layer of such a material cast on the aforementioned surface.

It is also known to bind enzymes to polymeric matrices. For example, in a cross-linked dextrose gel, adjacent hydroxyl groups can react with cyanogen bromide and then combine with amino groups of the enzyme. Other systems for incorporating enzymes into the matrix of a polymer are also known.

In an alternative embodiment, a mordant for the colored moiety produced in the present invention is employed. This would provide a degree of immobility to the colored species rendering the visual comparison more effective and accurate and still further lessening time of examination as a factor. The use of a mordant would also minimize any reversible reaction which might lead to inaccuracy in the determination. Mordants are well known to the art for a variety of colored materials and the particular mordant will be selected with the particular colored material in mind.

As stated above, the novel device of the present invention is suitable for use in a variety of diagnostic tests. In the following table, representative substances to be analyzed are indicated with examples of specific enzymes required for the determination.

| Substance | Enzymes |
| --- | --- |
| Glucose | Hexokinase |
|  | Glucose-6-phosphate dehydrogenase |
| Alcohol | Alcohol dehydrogenase |
| Triglycerides | Glycerol kinase |
|  | Pyruvate kinase |
|  | Lactate dehydrogenase |
| Blood urea nitrogen | Urease |
|  | l-glutarate dehydrogenase |
| Aldolase | Triosephosphate isomerase |
|  | Glyceraldehyde-3-phosphate dehydrogenase (GDH) |
| Creatine phosphokinase | Hexokinase |
|  | Glucose-6-phosphate dehydrogenase |
| Glutamate-oxalacetate transaminase | Malate dehydrogenase |

What is claimed is:

1. A device for determining concentration of a substance in a fluid which comprises fluid absorbing means carrying a substantially non-swellable, absorbent material of constant porosity and thickness; a first and second sheet which are carrying a predetermined amount of reagents adapted to react with said substance to provide a visual indication of the concentration of said substance; at least one of said first and second sheets is transparent; said fluid absorbing means intermediate and pivotally secured at each end to said first and second sheets adapted to be moved to a first superposed position where said reagents and said substance coact; said fluid absorbing means and said first and second sheets adapted to be moved to a second superposed position to contact means for generating the visual indication of the concentration of said substance.

2. The device of claim 1 wherein said reagents comprise enzymes, coenzymes and said means for generating the visual indication of the concentration of said substance comprise colorimetric indicators.

3. The device of claim 1 wherein said absorbent fluid means comprises a microporous filter.

4. The device of claim 1 wherein said fluid comprises blood.

5. The device of claim 4 wherein said reactants comprise hexokinase, glucose-6-phosphate dehydrogenase, nicotinamide adenine dinucleotide phosphate and adenosine triphosphate.

6. The device of claim 2 wherein said colorimetric indicator is incorporated in a precipitation chromatographic sheet.

7. The device of claim 1 wherein one of said transparent sheets includes a scale indicating concentration standards for said substance.

8. The device of claim 1 which includes means for removing undesirable components from said fluid prior to contacting said reagents with said fluid.

* * * * *